United States Patent [19]

Fonteyne

[11] Patent Number: 6,080,456

[45] Date of Patent: *Jun. 27, 2000

[54] PACKAGING FOR ARTICLES THAT ARE TO BE STERILIZED

[75] Inventor: Gerard Fonteyne, Evergem, Belgium

[73] Assignee: Horst Von Borries, Kerfeld, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/718,578

[22] PCT Filed: Jul. 19, 1995

[86] PCT No.: PCT/EP95/02850

§ 371 Date: Oct. 2, 1996

§ 102(e) Date: Oct. 2, 1996

[87] PCT Pub. No.: WO96/04861

PCT Pub. Date: Feb. 22, 1996

[30] Foreign Application Priority Data

Aug. 10, 1994 [DE] Germany .............................. 44 28 291

[51] Int. Cl.⁷ ...................................................... B32B 1/08
[52] U.S. Cl. ......................... 428/35.7; 428/513; 428/514
[58] Field of Search ................................... 428/35.7, 513, 428/514

[56] References Cited

U.S. PATENT DOCUMENTS

| | | | |
|---|---|---|---|
| 3,664,912 | 5/1972 | Olson | 161/161 |
| 4,623,587 | 11/1986 | Ito | 428/335 |
| 4,704,323 | 11/1987 | Duncan | 428/286 |
| 4,810,541 | 3/1989 | Newman et al. | 428/36.7 |
| 5,223,311 | 6/1993 | Tsutsumi | 428/513 |
| 5,234,750 | 8/1993 | Akao | 428/514 |
| 5,294,482 | 3/1994 | Gessner | 428/287 |
| 5,342,662 | 8/1994 | Aoyama | 428/514 |
| 5,654,091 | 8/1997 | Kiriazis | 428/332 |

FOREIGN PATENT DOCUMENTS

| | | |
|---|---|---|
| 0 056 323 | 7/1982 | European Pat. Off. . |
| 0 127 466 | 12/1984 | European Pat. Off. . |
| 0 437 856 | 7/1991 | European Pat. Off. . |
| 2 001 928 | 2/1977 | United Kingdom . |
| 2 070 514 | 9/1981 | United Kingdom . |

*Primary Examiner*—Paul R. Michl
*Attorney, Agent, or Firm*—Venable; Gabor Kelemen; Ashley J. Wells

[57] ABSTRACT

Packaging for a medical article to be gas-sterilized includes a plastic film which includes at least one layer and which is structured as a dome to house the medical article in use; and a plastic-treated paper web which is comprised of a paper web, which forms a pack base, and which is sealed to the plastic film in a peelable manner in use, wherein the paper web has a basis weight ranging between 55 and 250 g/m² and has been treated with a plastic so that the plastic-treated paper web has an average gas-permeability of at least 0.50 µm/Pa.s, and wherein the plastic is present in a weight ranging from 3 to 20 g/m² so that the packaging after sealing in use may be opened without contaminating the medical article contained therein with fibers from the paper web.

12 Claims, 6 Drawing Sheets

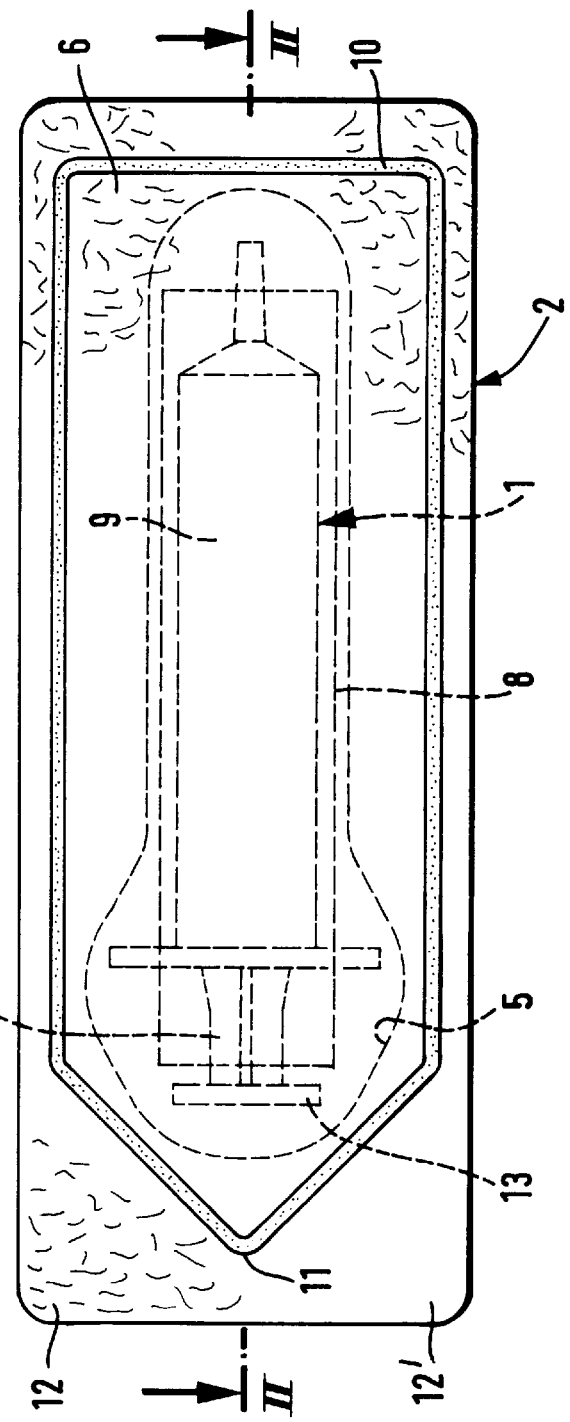
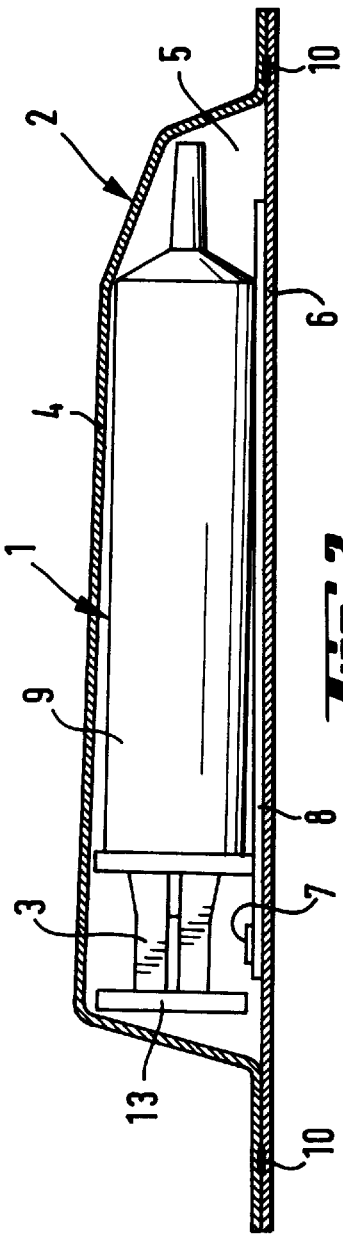

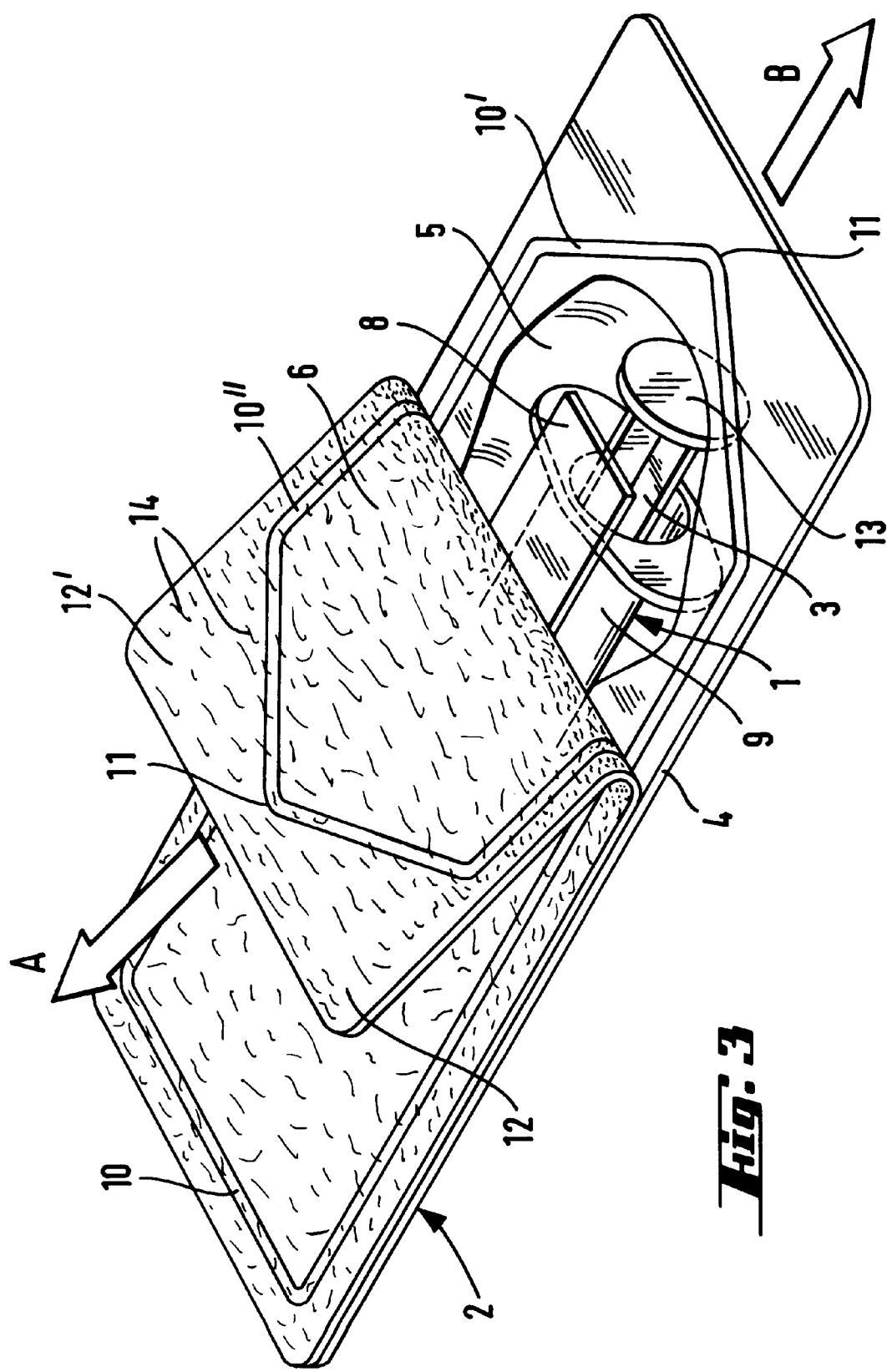

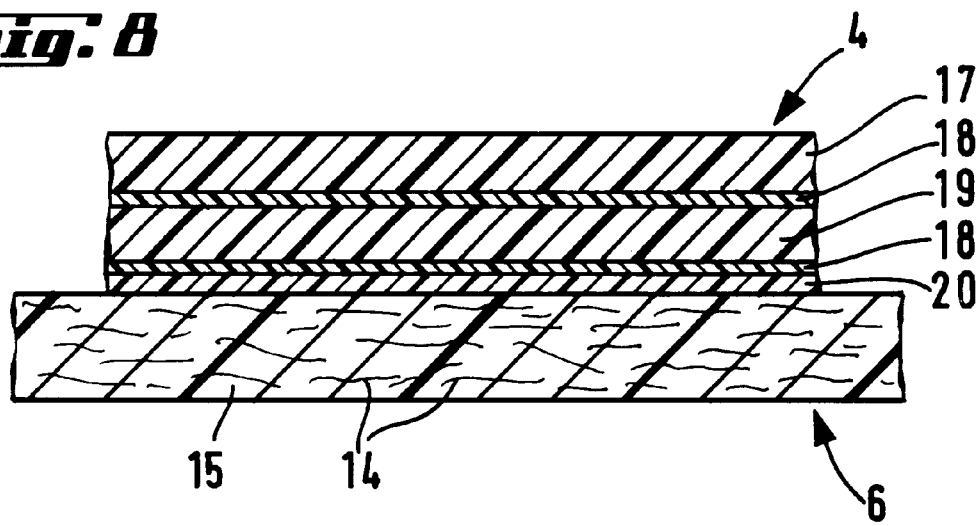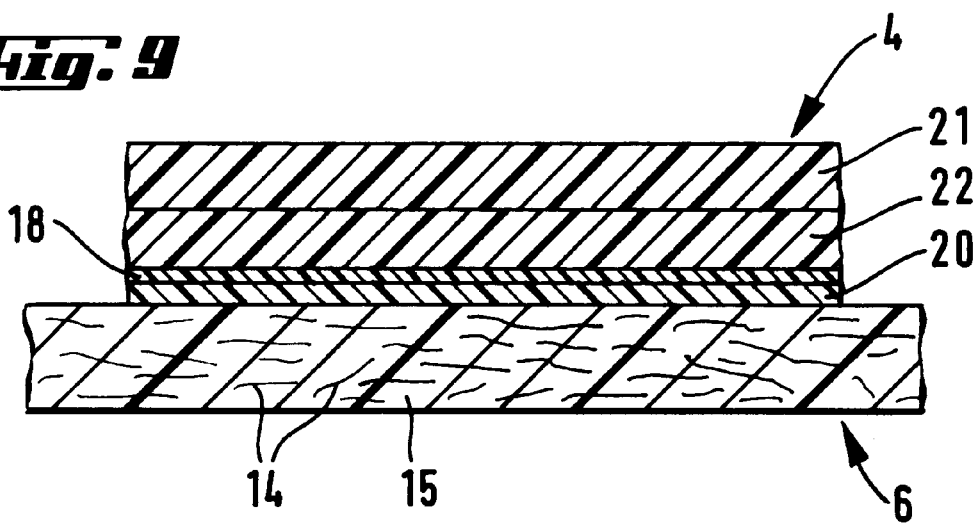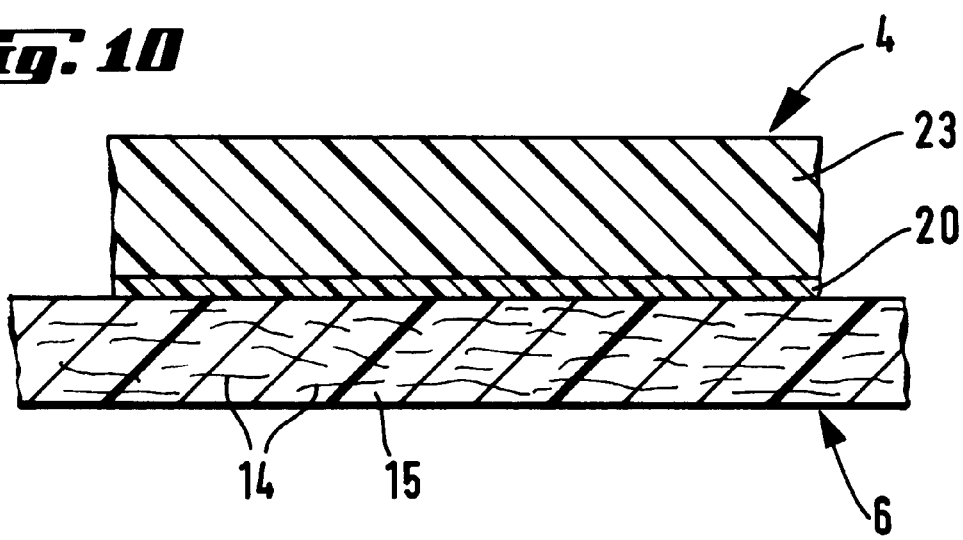

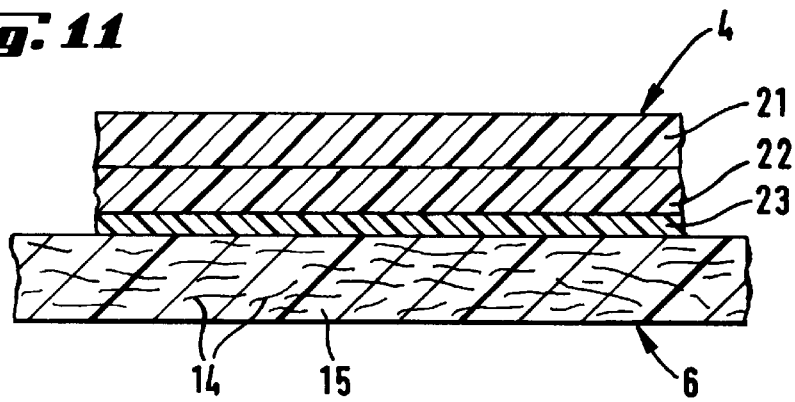
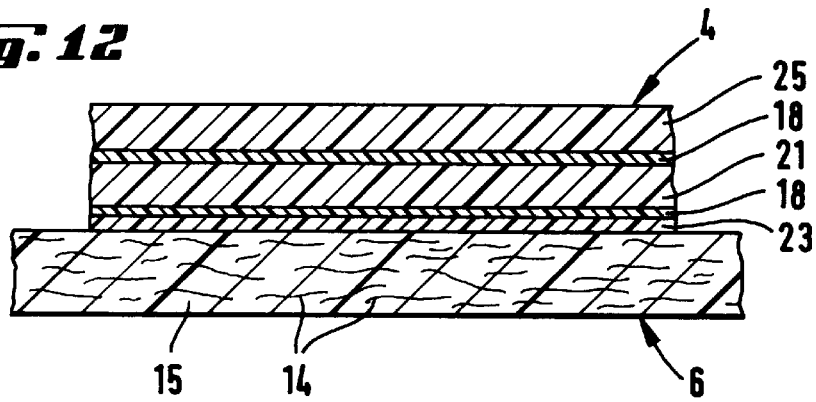
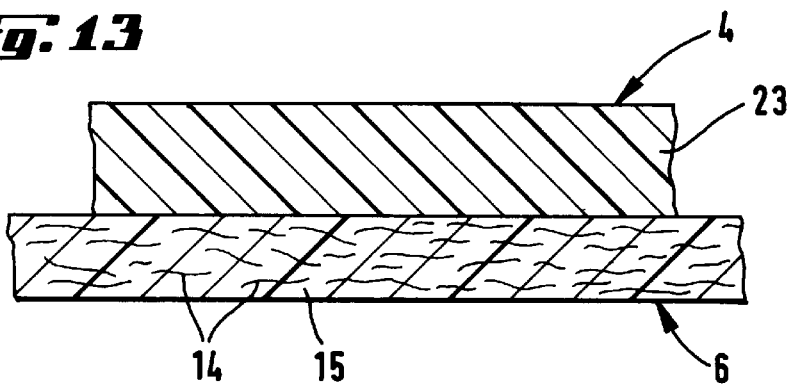
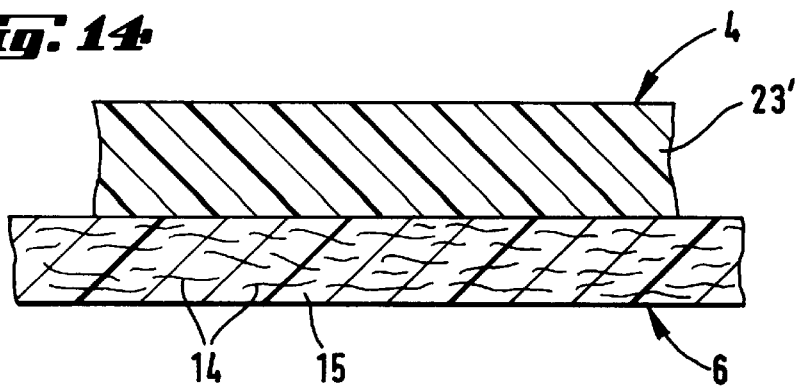

PACKAGING FOR ARTICLES THAT ARE TO BE STERILIZED

BACKGROUND OF THE INVENTION

1. Field of the Invention

The invention relates to a pack for articles to be sterilized, comprising an optionally thermoformed plastic film forming a dome, and a paper web forming the pack base, where the paper web has been heat-sealed to the film in a peelable manner.

2. Description of the Related Art

Packs containing sterile articles are disclosed, for example, in DE 8706916 U1, which reveals that a plastic film web having thermoformed recesses is heat-sealed to a paper web in a peelable manner, the paper web being gas-permeable so that the articles can be sterilized after packing by pressure treatment with germicidal gas.

U.S. Pat. No. 4,810,541-A discloses a heat-sealable food container which is covered by a foil lid. The container as such is a thermoformed plastic moulding of a multilayer film. The inner layer of the container is conceived as a peel layer and comprises a mixture of polyethylene, ethylene-vinyl acetate copolymer and butene polymer. The foil lid is an aluminium foil coated on both sides, and the outer layer comprises polyester, the inner layer, facing the contents, comprises polyethylene. The peel layer is heat-sealed to the polyethylene layer of the lid during sealing of the container. The problem of gas sterilization of the contents is not discussed.

DE 1927746 discloses a pack for sterilized articles which comprises a plastic container with an opening, where the opening is covered by a plastic-impregnated, moisture-impermeable, germ-free paper. The synthetic resin employed for the paper impregnation is a polyacrylate, polyester or polyvinyl alcohol. The reverse of the paper is additionally provided with a polyethylene or ethylene-vinyl acetate copolymer hot-melt adhesive coating.

WO 8603976 describes a sterile pack which comprises inner and outer wrappers. The outer wrapper allows gas sterilization of the inner wrapper and the contents thereof, and subsequently the outer wrapper is heat-sealed so that the contents remain bacteria-free.

The great disadvantage of these and similar constructions of the prior art is that on opening the packs, which is generally carried out by the peel method, i.e. by peeling the plastic film off from the paper web, the plastic film tears fibres out of the paper web and thus contaminates the sterile pack contents. Thus, the constructions of the prior art do not allow a sterile pack comprising paper and plastic film to be opened in such a way that no fibres and/or fibre fragments are released.

The object of the invention is therefore to enable a gas-sterilizable pack to be opened in such a way that no fibres are torn off from the paper, i.e. the opening is carried out entirely free from fibres, although the film is peeled off by the peel method.

SUMMARY OF THE INVENTION

This object is achieved in a pack for articles to be sterilized, comprising an optionally thermoformed plastic film forming a dome, and a paper web forming the pack base, where the paper web is heat-sealed to the film in a peelable manner, characterized in that the plastic film (4) is a multilayer film whose side facing the paper (6) is a copolymer comprising a) at least one ethylene polymer and/or ethylene-vinyl acetate copolymer, and b) a styrene homopolymer, and/or c) an elastomeric polymer; where a) is present in an amount of 55–95 per cent by weight as a polyethylene polymer having a density of from 0.91 to 0.93 g/ccm and a melt flow index of from 0.5 to 7.0 g/10 min, and the ethylene-vinyl acetate copolymer contains a maximum of 10 per cent by weight of vinyl acetate;

b) the styrene homopolymer is present in an amount of from 0 to 30 per cent by weight;

c) an elastomeric, thermoplastic styrene-butadiene-styrene block copolymer or styrene-isoprene-styrene block copolymer is present in an amount of from 0 to 20 per cent by weight and/or a polybutylene or polyisobutylene polymer is present in an amount of from 0 to 30 per cent by weight;

the paper of the pack base is plastic-treated paper having a mean gas permeability of at least 0.50 $\mu$m/Pa.s; and the plastic film is heat-sealed to the paper web.

DESCRIPTION OF THE PREFERRED EMBODIMENTS

The basis weight of the paper is preferably from 55 to 250 g/m$^2$, the weight of the plastic coating is from 3 to 20 g/m$^2$, and the plastic is preferably an EVA copolymer.

The plastic laminate is expediently produced by coextrusion, but can also be manufactured by adhesive lamination with a mono- or coextruded film. It preferably has a five-layer structure, i.e. an adhesion promoter layer is arranged above the peel layer facing the paper and bonds a polyamide layer to the peel layer and is itself bonded to a polyethylene layer by a further adhesion promoter layer.

The polyamide layer can expediently also be replaced by a styrene homopolymer or copolymer layer; in these cases, the polyethylene/polyamide or polyethylene/polystyrene combination serves as stabilizing constituent for the thermoforming.

It is furthermore possible to use HD or LD polyethylene and copolymers (EVA, LLDPE, EBA, EMA, EAA, etc.) instead of polyamide. Success has also been achieved using films made from polycarbonate, polyester, copolyester and polyvinyl chloride.

The adhesion promoter arranged between the individual layers is preferably an EVA copolymer or an EAA terpolymer.

In a further expedient embodiment of the invention, the laminate comprises the peel layer bonded via a lamination adhesive to an LDPE film and an HDPE film laminated thereon. This film combination is also readily thermoformable and has good dimensional stability.

The plastic expediently applied to only one side of the paper is preferably an EVA copolymer and, in a particularly preferred embodiment of the invention, extends essentially over the entire paper thickness, i.e. the plastic essentially penetrates through the paper on application thereto, producing strong binding of the fibres without the porosity being significantly reduced.

The paper advantageously comprises a coarse grade of pulp which, in a further expedient embodiment of the invention, has not been beaten or has not been beaten significantly. In combination with the further advantageous feature that the paper is an unfilled paper, i.e. contains no pigments, the high air permeability desired is ensured and simultaneously high strength is achieved.

In a preferred embodiment of the invention, this strength is further increased by sprinkling the paper using sodium silicate.

A very advantageous embodiment of the invention proposes that the plastic film is optionally a multilayer film whose side facing the paper is a polypropylene or a polypropylene copolymer; the paper of the pack base is a plastic-treated paper which has a mean gas permeability of at least 0.50 μm/Pa.s and a basis weight of from 55 to 250 g/m², the plastic coating has a weight of 3–20 g/m², and the plastic is an EVA copolymer which is applied to one side of the paper (6) and extends essentially over the entire paper thickness.

EXAMPLE 1

Sterile packs for packing disposable syringes were produced on a commercially available Tiromat 3000 automatic moulding and packing machine. The individual sterile pack had a size of 44×125 mm and comprised a club-shaped recess with a length of about 100 mm and a radius of 15 mm at the thicker and a radius of 5 mm at the thinner end. The film used was a commercially available polyamide-polyethylene composite film having a thickness of 95 μm. The roll width was 465 mm, and the roll length was 900 m. 10 packs could be accommodated on a roll width. The machine speed was 300 packs per minute. The moulding temperature for the film was 115° C.

The thermoforming of the recesses was carried out using compressed air at 5 bar. After introduction of the disposable syringes, a commercially available medical paper was fed over the PA-PE composite film, pressed against it and heat-sealed to the plastic film in the contour area of the lands. The heat-sealing temperature was 180° C., the sealing time was 1 second. The medical paper had a weight of 60 g/cm². Heat-sealing gave a strong, leak-proof bond between the composite film and the medical paper. After separation of the sterile packs produced into individual packs, they were sterilized for 7 hours at a temperature of 45–50° C. and from 50 to 60% atmospheric humidity in an autoclave with a capacity of 40 cubic meters. The sterilization medium used was ethylene oxide gas in a concentration of 800 mg/l. The sterilization marks arranged in some packs indicated that the sterilization had been successful.

On opening individual packs, it was found that fibres which had been in the weld seam region had been torn out of the medical paper; some of these fibres and fibre fragments were loose and fell onto the disposable syringe, while other fibres stuck more or less strongly to the heat-sealing layer of the multilayer film.

EXAMPLE 2

Example 1 was modified by replacing the commercially available medical paper and the commercially available composite film by the paper and film of the invention. The plastic film here was a five-layer laminate, having an outer layer of polyamide, an adhesive layer applied thereto, then a polyethylene layer, then an adhesive layer and, on the side facing the paper, a peel layer. Both adhesive layers comprised an ethylene-vinyl acetate copolymer. The peel layer had the following composition: 70 per cent by weight of polyethylene having a density of 0.922 g/ccm, and a melt flow index of 0.85 g/10 min, 20 per cent by weight of styrene homopolymer and 10 per cent by weight of styrene-butadiene-styrene block copolymer.

The paper had a basis weight of 62.5 g/m², the weight of the plastic coating was 3 g/m², the plastic applied was an EVA copolymer, and the mean gas permeability of the paper was 2.2 μm/Pa.s.

The sterilization was carried out analogously to Example 1. No paper fibres were detached from the paper when the pack was torn open. A clear mark in the form of a white line on the peel film was evident in the seal area, i.e. visible evidence that the pack had been opened.

EXAMPLE 3

The sterile pack was produced analogously to Example 1, but the plastic film was a five-layer material as in Example 2. The peel layer had the following composition: 90 per cent by weight of polyethylene having a density of 0.922 g/ccm and a melt flow index of 0.85 g/10 min, and 10 per cent by weight of styrene homopolymer.

The paper had a basis weight of 62.5 g/m², the weight of the plastic coating was 3 g/m², the plastic applied was an EVA copolymer, and the mean gas permeability was 2.2 μm/Pa.s.

The sterilization was carried out analogously to Example 1. No paper fibres were detached from the paper when the packs were torn open.

EXAMPLE 4

The sterile pack was produced analogously to Example 1, but the plastic film was a five-layer material as in Example 2. The peel layer had the following composition: 70 per cent by weight of polyethylene having a density of 0.944 g/ccm and a melt flow index of 0.17 g/10 min, 20 per cent by weight of styrene homopolymer and 10 per cent by weight of styrene-butadiene-styrene block copolymer.

The paper had a basis weight of 62.5 g/m², the weight of the plastic coating was 3 g/m², the plastic applied was an EVA copolymer, and the mean gas permeability of the paper was 2.2 μm/Pa.s.

The sterilization was carried out analogously to Example 1. No paper fibres were detached from the paper when the packs were torn open. A clear mark in the form of a white line on the peel film was evident in the seal area, i.e. visible evidence that the pack had been opened.

EXAMPLE 5

The sterile pack was produced analogously to Example 1, but the plastic film was a five-layer material as in Example 2. The peel layer had the following composition: 65 per cent by weight of polyethylene having a density of 0.928 g/ccm and a melt flow index of 1.6 g/10 min, ethylene-vinyl acetate copolymer containing 4 per cent by weight of vinyl acetate, 20 per cent by weight of styrene homopolymer and 15 per cent by weight of styrene-butadiene-styrene block copolymer.

The paper had a basis weight of 104.5 g/m², the weight of the plastic coating was 3.5 g/m², the plastic applied was an EVA copolymer, and the mean gas permeability of the paper was 1.2 μm/Pa.s.

The sterilization was carried out analogously to Example 1. No paper fibres were detached from the paper when the packs were torn open. A clear mark in the form of a white line on the peel film was evident in the seal area, i.e. visible evidence that the pack had been opened.

EXAMPLE 6

The sterile pack was produced analogously to Example 1, but the plastic film was a five-layer material as in Example 2. The peel layer had the following composition: 68 per cent by weight of polyethylene having a density of 0.923 g/ccm and a melt flow index of 0.3 g/10 min, 20 per cent by weight of styrene homopolymer and 12 per cent by weight of styrene-isoprene-styrene block copolymer.

The paper had a basis weight of 104.5 g/m$^2$, the weight of the plastic coating was 3.5 g/m$^2$, the plastic applied was an EVA copolymer, and the mean gas permeability of the paper was 1.2 μm/Pa.s.

The sterilization was carried out analogously to Example 1. No paper fibres were detached from the paper when the packs were torn open. A clear mark in the form of a white line on the peel film was evident in the seal area, i.e. visible evidence that the pack had been opened.

EXAMPLE 7

The experimental set-up was analogous to that in Example 2, but a three-layer film was employed whose outer layer comprised EDPE film, the middle layer comprised LDPE film and the peel layer comprised 70 per cent by weight of polyethylene having a density of 0.944 g/ccm and a melt flow index of 0.17 g/10 min, 20 per cent by weight of styrene homopolymer and 10 per cent by weight of styrene-butadiene-styrene block copolymer. The film was not thermoformed; sterile cloths were packed in flat bags.

The paper had a basis weight of 62.5 g/m$^2$, the weight of the plastic coating was 3 g/m$^2$, the plastic applied was an EVA copolymer, and the mean gas permeability of the paper was 2.2 μm/Pa.s.

The sterilization was carried out analogously to Example 1. No paper fibres were detached from the paper when the packs were torn open. A clear mark in the form of a white line on the peel film was evident in the seal area, i.e. visible evidence that the pack had been opened.

EXAMPLE 8

The sterile pack was produced analogously to Example 1, but the plastic film was a five-layer material as in Example 2. The peel layer had the following composition: 80 per cent by weight of polyethylene having a density of 0.922 g/ccm and a melt flow index of 0.85 g/10 min, and 20 per cent by weight of polybutylene.

The paper had a basis weight of 62.5 g/m$^2$, the weight of the plastic coating was 3 g/m$^2$, the plastic applied was an EVA copolymer, and the mean gas permeability of the paper was 2.2 μm/Pa.s.

The sterilization was carried out analogously to Example 1. No paper fibres were detached from the paper when the packs were torn open.

EXAMPLE 9

The sterile pack was produced analogously to Example 1, but the plastic film was a five-layer material as in Example 2. The peel layer had the following composition: 95 per cent by weight of polyethylene having a density of 0.923 g/ccm and a melt flow index of 0.86 g/10 min, and 5 per cent by weight of polybutylene.

The paper had a basis weight of 62.5 g/m$^2$ the weight of the plastic coating was 3 g/m$^2$, the plastic applied was an EVA copolymer, and the mean gas permeability of the paper was 2.2 μm/Pa.s.

The sterilization was carried out analogously to Example 1. No paper fibres were detached from the paper when the packs were torn open.

EXAMPLE 10

The sterile pack was produced analogously to Example 1, but the plastic film was a five-layer material as in Example 2. The peel layer had the following composition: 90 per cent by weight of polyethylene having a density of 0.925 g/ccm and a melt flow index of 2.0 g/10 min, and 10 per cent by weight of polyisobutylene.

The paper had a basis weight of 62.5 g/m$^2$, the weight of the plastic coating was 3 g/m$^2$, the plastic applied was an EVA copolymer, and the mean gas permeability of the paper was 2.2 μm/Pa.s.

The sterilization was carried out analogously to Example 1. No paper fibres were detached from the paper when the packs were torn open.

EXAMPLE 11

The sterile pack was produced analogously to Example 1, but the plastic film was a five-layer material as in Example 2. The peel layer had the following composition: 45 per cent by weight of polyethylene having a density of 0.922 g/ccm and a melt flow index of 0.85 g/10 min, 45 per cent by weight of ethylene-vinyl acetate copolymer containing 4 per cent by weight of vinyl acetate having a density of 0.925 g/ccm and a melt flow index of 0.5 g/10 min, and 15 per cent by weight of polybutylene.

The paper had a basis weight of 62.5 g/m$^2$, the weight of the plastic coating was 3 g/m$^2$, the plastic applied was an EVA copolymer, and the mean gas permeability of the paper was 2.2 μm/Pa.s.

The sterilization was carried out analogously to Example 1. No paper fibres were detached from the paper when the packs were torn open. A clear mark in the form of a white line on the peel film was evident in the seal area, i.e. visible evidence that the pack had been opened.

EXAMPLE 12

The sterile pack was produced analogously to Example 1, but the plastic film was a five-layer material as in Example 2. The peel layer had the following composition: 70 per cent by weight of polyethylene having a density of 0.923 g/ccm and a melt flow index of 0.85 g/10 min, 20 per cent by weight of styrene homopolymer and 10 per cent by weight of styrene-butadiene-styrene block copolymer.

The paper had a basis weight of 62.5 g/m$^2$, the weight of the plastic coating was 3 g/m$^2$, the plastic applied was an EVA copolymer, and the mean gas permeability of the paper was 2.2 μm/Pa.s.

The sterilization was carried out analogously to Example 1. No paper fibres were detached from the paper when the packs were torn open. A clear mark in the form of a white line on the peel film was evident in the seal area, i.e. visible evidence that the pack had been opened.

EXAMPLE 13

The sterile pack was produced analogously to Example 1, but the plastic film was a five-layer material as in Example 2. The peel layer had the following composition: 70 per cent by weight of polyethylene having a density of 0.923 g/ccm and a melt flow index of 0.85 g/10 min, 20 per cent by weight of styrene homopolymer and 10 per cent by weight of styrene-butadiene-styrene block copolymer.

The paper had a basis weight of 62.5 g/m$^2$, the weight of the plastic coating was 3 g/m$^2$, the plastic applied was an EVA copolymer, in addition 2.5 per cent by weight of sodium silicate, and the mean gas permeability of the paper was 2.2 μm/Pa.s.

The sterilization was carried out analogously to Example 1. No paper fibres were detached from the paper when the packs were torn open. A clear mark in the form of a white line on the peel film was evident in the seal area, i.e. visible evidence that the pack had been opened.

EXAMPLE 14

In an experimental set-up analogous to that in Example 2, a multilayer film was employed whose outer layer comprised a 12 μm, bioriented polyester film bonded to a coextruded peel film by adhesive lamination. The peel film comprised three layers, a plasma-treated LDPE layer, an adhesive layer based on polyethylene or ethylene-vinyl acetate copolymer, and the peel layer having the following composition: 70 per cent by weight of polyethylene having a density of 0.944 g/ccm and a melt flow index of 0.17 g/10 min, 20 per cent by weight of styrene homopolymer and 10 per cent by weight of styrene-butadiene-styrene block copolymer. The multilayer film was not thermoformed, but instead converted into flat bags.

The paper had a basis weight of 62.5 g/m$^2$, the weight of the plastic coating was 3 g/m$^2$, the plastic applied was an EVA copolymer, and the mean gas permeability of the paper was 2.2 μm/Pa.s.

The sterilization was carried out analogously to Example 1. No paper fibres were detached from the paper when the packs were torn open. A clear mark in the form of a white line on the peel film was evident in the seal area, i.e. visible evidence that the pack had been opened.

EXAMPLE 15

Example 1 was modified by replacing the commercially available medical paper and the commercially available composite film by the paper and film of the invention. The plastic film here was a five-layer laminate, having an outer layer of polyamide, an adhesive layer applied thereto, then a polyethylene layer, then an adhesive layer and, on the side facing the paper, a polypropylene layer. The paper had a basis weight of 62.5 g/m$^2$, the weight of the plastic coating was 3 g/m$^2$, the plastic applied was an EVA copolymer, and the mean gas permeability of the paper was 2.2 μm/Pa.s.

The sterilization was carried out analogously to Example 1. No paper fibres were detached from the paper when the pack was torn open.

EXAMPLE 16

The sterile pack was produced analogously to Example 1, but the plastic film was a five-layer material as in Example 2. The peel layer comprised a polypropylene copolymer. The paper had a basis weight of 62.5 g m$^2$, the weight of the plastic coating was 3 g/m$^2$, the plastic applied was an EVA copolymer, and the mean gas permeability of the paper was 2.2 μm/Pa.s.

The sterilization was carried out analogously to Example 1. No paper fibres were detached from the paper when the packs were torn open.

EXAMPLE 17

The experimental set-up was analogous to that in Example 2, but a three-layer film was employed whose outer layer comprised HDPE film, the middle layer comprised LDPE film and the peel layer comprised polypropylene having a density of 0.905 g/ccm and a melt flow index of 2.00 g/10 min. The film was not thermoformed; sterile cloths were packed in flat bags.

The paper had a basis weight of 62.5 g/m$^2$, the weight of the plastic coating was 3 g/m$^2$, the plastic applied was an EVA copolymer, and the mean gas permeability of the paper was 2.2 μm/Pa.s.

The sterilization was carried out analogously to Example 1. No paper fibres were detached from the paper when the packs were torn open.

EXAMPLE 18

The sterile pack was produced analogously to Example 1, but the plastic film was a 40 μm single-layer polypropylene film having a density of 0.905 g/ccm and a melt flow index of 4.00 g/10 min.

The paper had a basis weight of 62.5 g/m$^2$, the weight of the plastic coating was 3 g/m$^2$, the plastic applied was an EVA copolymer, and the mean gas permeability of the paper was 2.2 μm/Pa.s.

The sterilization was carried out analogously to Example 1. No paper fibres were detached from the paper when the packs were torn open.

EXAMPLE 19

The sterile pack was produced analogously to Example 1, but the plastic film was a 25 μm single-layer propylene copolymer material having a density of 0.900 g/ccm and a melt flow index of 6.00 g/10 min.

The paper had a basis weight of 62.5 g/m$^2$, the weight of the plastic coating was 3 g/m$^2$, the plastic applied was an EVA copolymer, and the mean gas permeability of the paper was 2.2 μm/Pa.s.

The sterilization was carried out analogously to Example 1. No paper fibres were detached from the paper when the packs were torn open.

EXAMPLE 20

In an experimental set-up analogous to that in Example 2, a multilayer film was employed whose outer layer comprised a 12 μm, bioriented polyester film bonded to a coextruded peel film by adhesive lamination. The peel film comprised three layers, a plasma-treated LDPE layer, an adhesive layer based on polyethylene or ethylene-vinyl acetate copolymer, and, as peel layer, polypropylene having a thickness of 20 μm, a density of 0.905 g/ccm and a melt flow index of 18.00 g/10 min.

The paper had a basis weight of 62.5 g/m$^2$, the weight of the plastic coating was 3 g/m$^2$, the plastic applied was an EVA copolymer, and the mean gas permeability of the paper was 2.2 μm/Pa.s.

The sterilization was carried out analogously to Example 1. No paper fibres were detached from the paper when the packs were torn open.

EXAMPLE 21

Example 1 was modified by replacing the commercially available medical paper and the commercially available composite film by the paper and film of the invention. The plastic film here was a five-layer laminate, having an outer layer of polyamide, an adhesive layer applied thereto, then a polyethylene layer, then an adhesive layer and, on the side facing the paper, a peel layer. Both adhesive layers comprised an ethylene-vinyl acetate copolymer. The peel layer had the following composition: 67 per cent by weight of polyethylene having a density of 0.922 g/ccm, and a melt flow index of 0.85 g/10 min, 3 per cent by weight of a masterbatch containing a contrast colour (blue), 20 per cent by weight of styrene homopolymer and 10 per cent by weight of styrene-butadiene-styrene block copolymer.

The paper had a basis weight of 62.5 g/m², the weight of the plastic coating was 3 g/m², the plastic applied was an EVA copolymer, and the mean gas permeability of the paper was 2.2 μm/Pa.s.

The sterilization was carried out analogously to Example 1. No paper fibres were detached from the paper when the pack was torn open. A clear blue mark in the form of a line on the paper was evident in the seal area, i.e. visible evidence that the pack had been opened.

BRIEF DESCRIPTION OF THE DRAWINGS

The invention is described below with reference to the drawings, in which:

FIG. 1 shows a plan view of a sterile pack

FIG. 2 shows a front section view of a sterile pack

FIG. 3 shows a side view of a partially opened pack

FIG. 8 shows a five-layer laminate in section

FIG. 9 shows a four-layer laminate in section

FIG. 10 shows a two-layer laminate in section

FIG. 11 shows a five-layer laminate in section

FIG. 12 shows a three-layer laminate in section

FIG. 13 shows a monofilm in section

FIG. 14 shows a monofilm in section.

The blister pack 2 has, as shown in FIGS. 1 and 2, an accommodation chamber 5 formed by thermoforming the film web 4 in this region. The accommodation chamber 5 accommodates the disposable syringe 1, which essentially comprises the piston 3 and the barrel 9. The accommodation chamber 5 is covered by the paper web 6, which is welded to the film web 4 along the seal seam 10. The seal seam 10 as, in the left-hand part of the blister pack 2, a corner 11, starting from which the blister pack 2 can be torn open by means of the tabs 12 and 12', i.e. the regions in which the film web 4 is only in loose contact with the paper web 6. As shown in FIG. 2, the blister pack 2 contains, in addition to the disposable syringe 1, an insert with instructions, to which the sterile mark 7 is also applied. After the film web 4 has been thermoformed, the disposable syringe 1 is thus first placed in the accommodation chamber 5 formed, the insert 8 with the instructions and the sterile mark 7 applied thereto is inserted on top, and the film web 4, i.e. the filled accommodation chambers 5 arranged alongside one another, is only then covered with the paper web 6 and welded.

Figure 4:
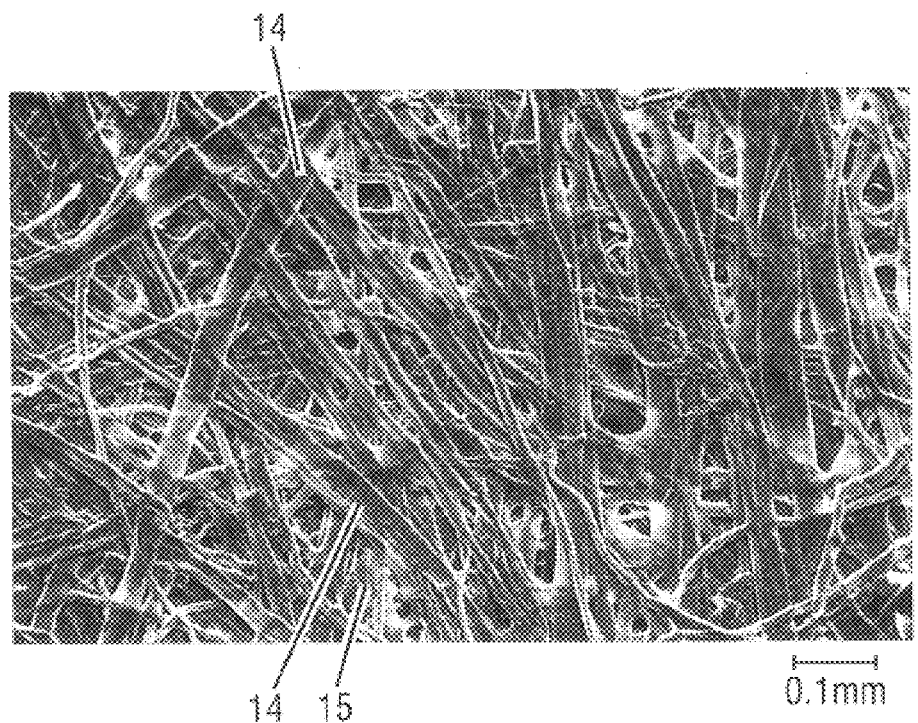
FIGS. 4 to 7 show scanning electron micrographs of the paper
Figure 5:
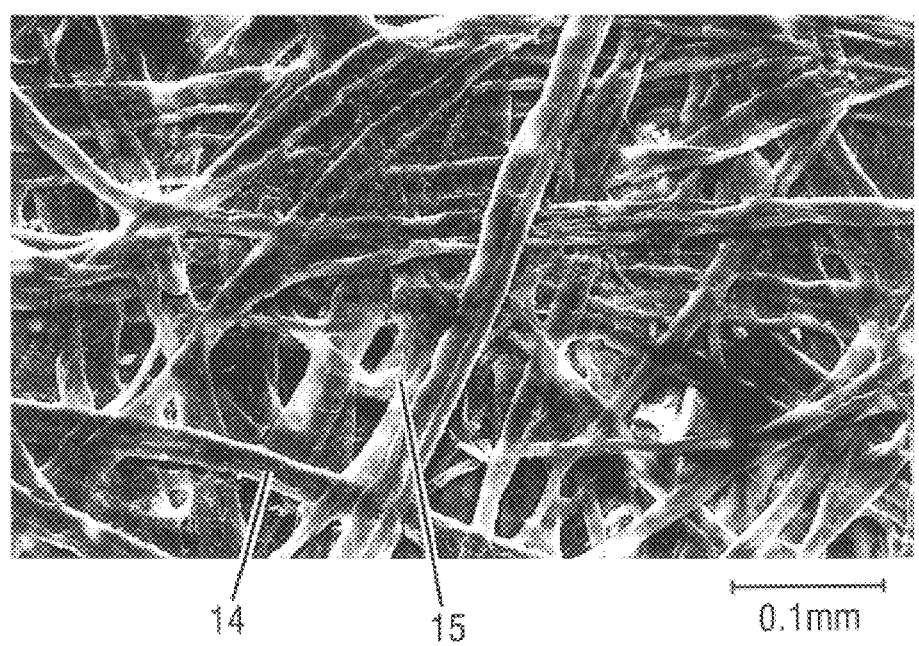
Figure 6:
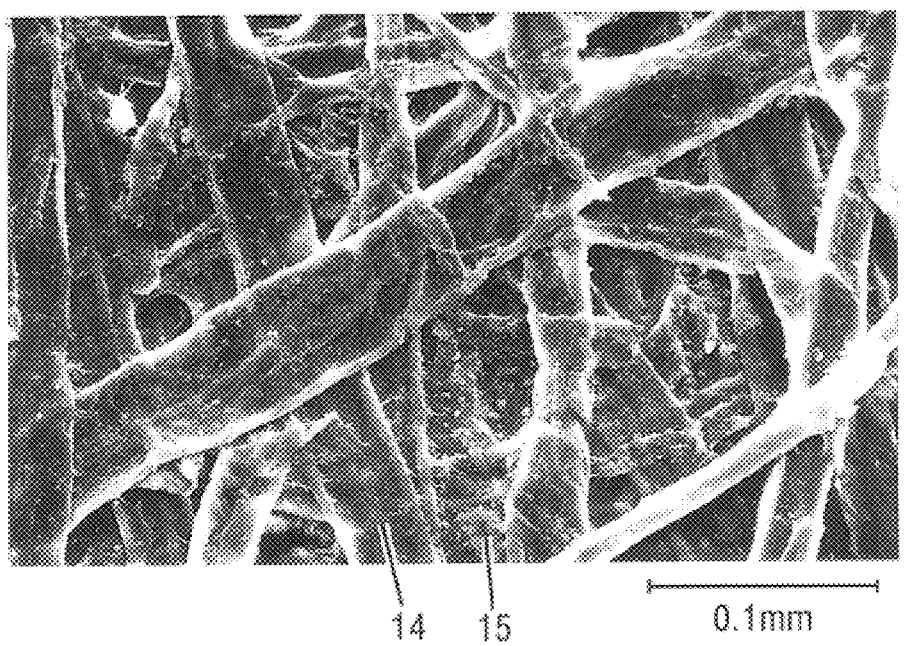

As shown by FIG. 3, the sterile pack 2 is opened by grasping the film web 4 and the paper web 6 in the region of the corner 11 of the weld seam 10 at the tabs 12, 12' and peeling them apart in the direction of arrows A and B. The plunger head 13 of the disposable syringe 1 is thus exposed and can be taken hold of in order to remove the disposable syringe from the pack.

As clearly shown in FIG. 3, the paper web 6 has paper fibres 14 distributed over the entire surface, i.e. including in the region of the sealed seam 10", whereas the seal seam 10', which is located on the film side, has no traces of adhering fibres 14.

Figure 7:
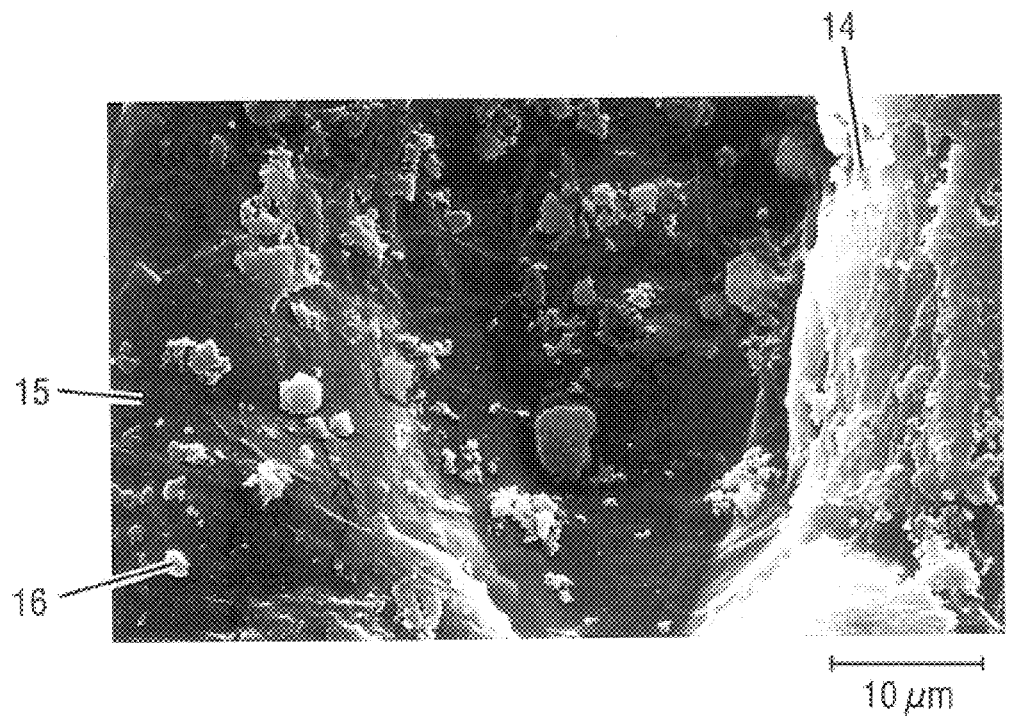

FIGS. 4–7 show that the fibres 14 are surrounded by plastic 15, at least in some areas. This plastic is an EVA copolymer. FIG. 7 additionally shows sodium silicate particles 16 distributed between the fibres 14.

FIGS. 8–10 show an enlargement of a section (transverse section) from a sealed pack. FIG. 8, which corresponds to Example 2, shows, in the outer layer, a polyamide film 17 which is bonded, via lamination with ethylene-vinyl acetate 18, to a polyethylene film 19. A peel film layer 20 is applied to the latter, likewise via an EVA lamination 18.

FIG. 9, which corresponds to Example 7, shows, as outer layer, an ED polyethylene film 21 produced by coextrusion with an LD polyethylene film 22. A peel film layer 20 is applied to the latter via an EVA lamination 18.

FIG. 10 shows, as outer layer, a polypropylene film 23 produced by coextrusion with a peel film 20.

FIGS. 11–13 show films in which the heat-sealing layer is formed by a polypropylene film 23.

FIG. 11 corresponds to Example 17, the outer layer comprising an HDPE film 21, the middle layer comprising an LDPE film 22 and the peel layer comprising polypropylene 23.

FIG. 12 corresponds to Example 20, the outer layer comprising a 12 μm bioriented polyester film 25, which is bonded to a coextruded peel film by adhesive lamination 18. The peel film comprises three layers, a plasma-treated LDPE layer 21, an adhesive layer based on ethylene-vinyl acetate copolymer 18 and, as peel layer, polypropylene 23 in a thickness of 20 μm.

FIG. 13 corresponds to Example 18, in which a single-layer polypropylene film 23 in a thickness of 40 μm forms the peel film.

FIG. 14 corresponds to Example 19, in which a single-layer material, polypropylene copolymer 23', forms the peel film. All films are heat-sealed to the paper web 6.

What is claimed is:

1. Packaging for a medical article to be gas-sterilized, comprising:

a plastic film which includes at least one layer and which is structured as a dome to house the medical article in use; and a plastic-treated paper web which is comprised of a paper web, which forms a pack base, and which is sealed to the plastic film in a peelable manner in use;

wherein the plastic film has a layer which faces the plastic-treated paper web and which is comprised of one of a polypropylene or a polypropylene copolymer; and wherein the paper web has a basis weight ranging between 55 and 250 g/m² and has been treated with a plastic so that the plastic-treated paper web has an average gas-permeability of at least 0.50 μm/Pa.s, and wherein the plastic is an EVA copolymer present in a weight ranging from 3 to 20 g/m², which plastic has been applied to one side of the paper web and extends substantially through the entire thickness of the paper web so that the packaging after sealing in use may be opened without contaminating the medical article contained therein with fibers from the paper web.

2. Packaging for a medical article to be gas-sterilized, comprising:

a plastic film which includes at least one layer and which is structured as a dome to house the medical article in use; and a plastic-treated paper web which is comprised of a paper web, which forms a pack base, and which is sealed to the plastic film in a peelable manner in use, wherein the paper web has a basis weight ranging between 55 and 250 g/m² and has been treated with a plastic which comprises an EVA copolymer so that the plastic-treated paper web has an average gas-permeability of at least 0.50 μm/Pa.s, and wherein the plastic is present in a weight ranging from 3 to 20 g/m² so that the packaging after sealing in use may be opened without contaminating the medical article contained therein with fibers from the paper web.

3. The packaging according to claim 2, wherein the plastic is applied to one side of the paper web.

4. The packaging according to claim 2, wherein the plastic extends substantially through the entire thickness of the paper web.

5. The packaging according to claim 2, wherein the paper web is composed of a coarse cellulose.

6. The packaging according to claim 2, wherein the paper web is composed of cellulose and wherein the cellulose is substantially unrefined.

7. The packaging according to claim 2, wherein the paper web is an unfilled paper.

8. The packaging according to claim 2, wherein the paper web is a treated paper which is strengthened with sodium water glass.

9. The packaging according to claim 2, wherein the plastic film is a multi-layer film and has a layer which faces the plastic-treated paper web and which is comprised of one of a polypropylene or a polypropylene copolymer.

10. The packaging according to claim 2, wherein the plastic film is a multi-layer film and has a layer which faces the plastic-treated paper web and which is comprised of a copolymer including (a), (b), and (c) as follows:

(a) at least one of an ethylene polymer and an ethylene vinyl acetate copolymer in which the ethylene vinyl acetate copolymer contains a maximum of 10 percent by weight of vinyl acetate, wherein (a) is present in an amount ranging from 55 to 95 percent by weight as polyethylene polymer having a density of 0.91 to 0.93 g/ccm and a melt flow index ranging from 0.5 to 7.0 g/10 min;

(b) at least one of a styrene homopolymer and an elastomeric polymer, wherein the styrene homopolymer is present in an amount ranging from of 0 to 30 percent by weight; and (c) at least one of;
   (i) an elastomeric thermoplastic styrene-butadiene-styrene block copolymer or a styrene-isoprene-styrene block copolymer present in an amount ranging from 0 to 20 percent by weight; and
   (ii) a polybutylene or a polyisobutylene polymer present in an amount ranging from 0 to 30 percent by weight.

11. The packaging according to claim 10, wherein the multi-layer plastic film is a coextrudate.

12. The packaging according to claim 10, wherein the multi-layer plastic film is a laminate.

* * * * *

UNITED STATES PATENT AND TRADEMARK OFFICE
CERTIFICATE OF CORRECTION

PATENT NO : 6,080,456
DATED : June 27, 2000
INVENTOR(S): Gerard Fonteyne et al

It is certified that error appears in the above-identified patent and that said Letters Patent are hereby corrected as shown below:

On the title page, item [75], Inventor: the second inventor's name should appear: --Horst von Borries, Kerfeld, Germany--.

Signed and Sealed this

Eighth Day of May, 2001

Attest:

NICHOLAS P. GODICI

Attesting Officer

Acting Director of the United States Patent and Trademark Office

UNITED STATES PATENT AND TRADEMARK OFFICE
CERTIFICATE OF CORRECTION

PATENT NO. : 6,080,456
DATED : June 27, 2000
INVENTOR(S) : Gerard Fonteyne

It is certified that error appears in the above-identified patent and that said Letters Patent is hereby corrected as shown below:

Title page,
Item [75], Inventor, "Horst von Borries, Kerfeld, Germany" (as inserted by Certificate of Correction issued May 8, 2001) should be vacated.
Item [73], Assignee, should read -- Horst von Borries, Krefeld, Germany --

Signed and Sealed this

Tenth Day of August, 2004

JON W. DUDAS
*Acting Director of the United States Patent and Trademark Office*